United States Patent [19]

Ueda et al.

[11] Patent Number: 5,607,622
[45] Date of Patent: Mar. 4, 1997

[54] OIL-IN-WATER CREAM BASE

[75] Inventors: Seishi Ueda, Ise; Kaoru Maeyama, Tsu; Nobuhide Tsuji; Masahiro Tsujide, both of Ise; Kazuyuki Kitagawa, Taki-gun, all of Japan

[73] Assignee: Mikimoto Pharmaceutical Co., Ltd., Mie-ken, Japan

[21] Appl. No.: 21,758

[22] Filed: Feb. 24, 1993

[30] Foreign Application Priority Data

Jun. 29, 1992 [JP] Japan ................................ 4-192685

[51] Int. Cl.$^6$ ............................ B01J 13/00; A61K 9/107
[52] U.S. Cl. ...................... 252/312; 252/315.5; 424/401; 514/941; 514/944
[58] Field of Search ................ 252/312, 315.2, 252/315.5; 424/401, 406; 514/944, 941

[56] References Cited

U.S. PATENT DOCUMENTS

| | | | |
|---|---|---|---|
| 3,920,883 | 11/1975 | Yamada et al. | 514/938 |
| 3,939,260 | 2/1976 | Lafon | 424/401 |
| 4,505,924 | 3/1985 | Taylor et al. | 514/859 |
| 4,533,254 | 8/1985 | Cook et al. | 252/314 |
| 4,585,650 | 4/1986 | Newberry, Jr. et al. | 424/73 |
| 4,767,741 | 8/1988 | Komor et al. | 252/308 |
| 4,830,765 | 5/1989 | Perricone et al. | 252/49.3 |
| 5,057,502 | 10/1991 | Walsh | 514/944 |

FOREIGN PATENT DOCUMENTS

| | | |
|---|---|---|
| 50-84628 | 7/1975 | Japan . |
| 58-124535 | 7/1983 | Japan . |
| 58-181718 | 10/1983 | Japan . |
| 60-25936 | 2/1985 | Japan . |
| 60-255719 | 12/1985 | Japan . |
| 86-12890 | 4/1986 | Japan . |
| 86-43323 | 9/1986 | Japan . |
| 57-38936 | 3/1992 | Japan . |
| 4-91018 | 3/1992 | Japan . |
| 4-149108 | 5/1992 | Japan . |

OTHER PUBLICATIONS

D. Myers, *Surfactant Science and Technology*, (VCH publishers, Inc., NY, NY, 1988) pp. 212–215.

*Primary Examiner*—Richard D. Lovering
*Assistant Examiner*—Daniel S. Metzmaier
*Attorney, Agent, or Firm*—Darby & Darby

[57] ABSTRACT

An oil-in-water type cream base containing a colloidal hydrous silicate and a polyethylene glycol having an average molecular weight of 1,000–10,000, and emulsified by means of a microfluidizer. Preferably, the cream base contains a crystalline cellulose. According to the present invention, the strong, safe and stable cream base having excellent sensuosity can be prepared without using a surface active agent which is not always safe for men.

12 Claims, No Drawings

OIL-IN-WATER CREAM BASE

BACKGROUND OF THE INVENTION

1. Field of the Invention

The present invention relates to a cream base which can be used to manufacture stable cosmetics having high safety for skin and stable medicines such as skin external remedies and the like.

2. Description of the Prior Art

Usually, in the case that a cream base, i.e., emulsion is prepared, emulsification is carried out by using a surface active agent. However, the surface active agent has the problem of safety, and therefore much effort has been made to decrease the amount of the surface active agent as much as possible.

In order to meet this requirement, researches have been intensively conducted, but any emulsion which is excellent in safety and sensuosity has not been obtained so far.

Thus, as one measure for obtaining the satisfactory emulsion, the utilization of a colloidal hydrous silicate has been attempted so as to increase a yield point of an aqueous phase and to thereby stabilize the emulsion.

The colloidal hydrous silicate has a small particle diameter and can easily penetrate through fine spaces, and so the silicate can provide the emulsion with strong adsorbability and strong adhesion. A pH of a 2% aqueous silicate dispersion is in the range of 8 to 10.5, and an apparent specific gravity thereof is in the range of 0.7 to 1.0.

This kind of colloidal hydrous silicate has been used as a viscosity increasing agent or an auxiliary emulsifier, but in the case that the colloidal hydrous silicate obtained by a conventional technique is singly used, problems of sensuosity and safety are still present.

Japanese Patent Application Laid-open No. Hei3-83909 has suggested one solution. This is a cream base comprising a synthetic bentonite and silicon oil. In this cream base, the addition of the silicon oil permits decreasing the amount of the synthetic bentonite to thereby reduce creaky sense which the synthetic bentonite has, and the viscosity increasing function of the silicon oil and the fine particles of the synthetic bentonite function to maintain the stability of emulsification.

Furthermore, Japanese Patent Application Laid-open No. Hei3-221290 has suggested a cream base comprising a fatty acid dextrin and a colloidal hydrous silicate.

In this cream base, affinity for oily components can be enhanced by the fatty acid moiety, and affinity for aqueous components can be also enhanced by the dextrin moiety, whereby the stability of the emulsion can be heightened.

In an emulsification method of the cosmetic, a rotary homogenizer has often been heretofore used.

In recent years, a high-pressure type homogenizer has been developed, and as a result, emulsification power can be increased. Above all, a microfluidizer described in U.S. Pat. No. 4,533,254 is excellent. However, even if this kind of homogenizer is used, the conventional problems of separation and stability are still present.

SUMMARY OF THE INVENTION

A first object of the present invention is to provide a cream base in which any surface active agent is not used so as to enhance safety for skin and which has a sufficiently excellent sensuosity and a good stability.

A second object of the present invention is to provide an oil-in-water type cream base having a hyaluronidase inhibiting function and a good stability.

That is, the present invention is as follows:

(1) An oil-in-water type cream base comprising a colloidal hydrous silicate and a polyethylene glycol, and emulsified by means of a microfluidizer.

(2) An oil-in-water type cream base comprising a colloidal hydrous silicate and a polyethylene glycol having an average molecular weight of 1,000–10,000, and emulsified by means of a microfluidizer.

(3) An oil-in-water type cream base comprising a colloidal hydrous silicate, a polyethylene glycol having an average molecular weight of 1,000–10,000 and a crystalline cellulose, and emulsified by means of a microfluidizer.

(4) An oil-in-water type cream base described in any one of the preceding paragraphs (1) to (3) wherein the amount of the colloidal hydrous silicate is 0.2–10.0% by weight based on the weight of an aqueous component, and the amount of the polyethylene glycol is 0.3–15.0% by weight based on the weight of the aqueous component.

DETAILED DESCRIPTION OF THE INVENTION

The present inventors have intensively repeated various experiments in order to solve the above-mentioned problems, and as a result, they have found that the problems can be solved by the prescriptions described in the preceding paragraph SUMMARY OF THE INVENTION. In consequence, the present invention has been completed.

The colloidal hydrous silicates which is used in the present invention are colloidal hydrous aluminum magnesium silicates, colloidal hydrous montmorillonites or smectites, colloidal hydrous saponites.

Since a colloidal hydrous silicate tends to be affected by an aqueous component, the amount of the colloidal hydrous silicate to be blended depends upon the prescription as well as a kind and a grade of colloidal hydrous silicate itself. However, it is in the range of 0.2–10.0% by weight, preferably 0.2–2.0% by weight based on the aqueous component.

A polyethylene glycol increases affinity for the aqueous component due to a polar group of its hydroxyl group and affinity for an oil component due to an ethylene moiety, and thus it contributes to the stabilization of an emulsion. However, the polyethylene glycol having a low molecular weight has problems of safety and emulsion state. Furthermore, this substance has a molecular weight distribution, and so its molecular weight is represented by an average molecular weight. Thus, the average molecular weight of the polyethylene glycol which is fit for the purpose of the present invention is in the range of 1,000–10,000. Since the polyethylene glycol also tends to be affected by the oil component, and the amount of the polyethylene glycol to be blended depends upon the prescription and the polymerization degree distribution of the polyethylene glycol itself. However, it is in the range of 0.3–15.0% by weight, preferably 0.5–4.0% by weight based on the aqueous component.

In addition, a crystalline cellulose can be blended with the above-mentioned components in order to improve the sensuosity of a cream base.

In the present invention, a usual emulsification process can be applied, but it has been found that the emulsification by the use of a microfluidizer described in U.S. Pat. No. 4,533,254 increases stability and safety.

This microfluidizer should be used under a treatment pressure of 700 kg/cm² or more under which its function can be performed.

The microfluidizer is an emulsion forming apparatus, in which an emulsion-forming liquid mixture is converted into plural sheet-like flows by elongated orifices and their leading edges are allowed to impinge at a high speed, so that the flows become low-pressure turbulent zones, whereby the emulsion can be formed. Needless to say, the stable emulsion cannot be obtained only by using the microfluidizer without any emulsifying agent, and it should be noted that when the microfluidizer is combined with such a prescription as in the present invention, the stable emulsion can be obtained. This technique is described in detail in U.S. Pat. No. 4,533,254.

The use of this microfluidizer and the use of such an optimum emulsion-forming liquid mixture as in the present invention permit the formation of the stable emulsion without employing an emulsifying agent such as a surface active agent, and therefore a cream base can be prepared in which safety for men is secured.

An average particle diameter of the cream is preferably 0.3 micron or less. When the average particle diameter is in excess of 0.3 micron, the cream tends to separate unpreferably. The utilization of the microfluidizer permits easily regulating the average particle diameter of dispersed liquid drops to 0.01 μm–0.2 μm.

As the other materials which can be contained in the oil-in-water cream base, there can be utilized materials which are used in the usual cream base. All of polyvalent alcohols can be utilized, but above all, glycerin is most preferable.

Furthermore, the content of an oil phase is preferably 40% or less.

The oil-in-water type cream base of the present invention can be mixed with raw materials of a medicine such as a skin external remedy or raw materials of a cosmetic, for example, a liquid oil such as squalane or jojoba oil, a solid oil such as beeswax or cetyl alcohol, various active agents, a humectant such as glycerin, 1,3-butylene glycol, and the mixture is then emulsified by means of the microfluidizer. The resultant emulsion is next formed into a desired conformation of a cosmetic, a skin external remedy or the like, for example, lotion, cream, milky lotion or pack in compliance with a purpose.

EXAMPLES

Now, the present invention will be described in detail in reference to examples, but the scope of the present invention should not be limited to these examples. In the examples, "part" and "parts" mean "part by weight" and "parts by weight", respectively, unless otherwise specified.

Example 1 (Cream)

| | pts. wt. |
|---|---|
| Group A: | |
| Squalane | 10.0 |
| Octyldodecyl myristate | 10.0 |
| Whale wax | 5.0 |
| Beeswax | 5.0 |
| Silicon | 0.5 |

-continued

| | pts. wt. |
|---|---|
| Group B: | |
| Purified water | 41.8 |
| 6% Aqueous colloidal hydrous aluminum magnesium silicate solution | 15.0 |
| Glycerin | 10.0 |
| Polyethylene glycol (average molecular weight 4,000) | 2.0 |
| Methyl paraoxybenzoate | 0.2 |
| Sodium hyaluronate | 0.5 |

The Groups A and B were separately weighed, followed by heating and dissolving. The group A was mixed with the group B with stirring, and the mixture was then treated with a microfluidizer M-110Y under a treatment pressure of 1,600 kG/cm².

Example 2 (Cream)

| | pts. wt. |
|---|---|
| Group A: | |
| Squalane | 10.0 |
| Octyldodecyl myristate | 10.0 |
| Beeswax | 1.0 |
| Batyl alcohol | 3.5 |
| Stearyl alcohol | 2.5 |
| Stearyl acid | 0.5 |
| Silicon | 0.5 |
| Group B: | |
| Purified water | 39.3 |
| 6% Aqueous colloidal hydrous montmorillonite solution | 10.0 |
| 2% Aqueous crystalline cellulose solution | 10.0 |
| Glycerin | 10.0 |
| Polyethylene glycol (average molecular weight 6,000) | 2.0 |
| Methyl paraoxybenzoate | 0.2 |
| Sodium hyaluronate | 0.5 |

The groups A and B were separately weighed, followed by heating and dissolving. The group A was mixed with the group B with stirring, and the mixture was then treated with a microfluidizer M-110Y under a treatment pressure of 1,600 kg/cm².

Comparative Example 1

The prescription of Example 1 was emulsified by a desk homomixer LR-1 made by Mizuho Industry Co., Ltd. to prepare a cream.

Comparative Example 2

A polyethylene glycol (average molecular weight=4,000) in the prescription of Example 1 was replaced with 1,3-butylene glycol to prepare a cream.

Comparative Example 3

A 6% aqueous colloidal hydrous aluminum magnesium silicate solution in the prescription of Example 1 was replaced with purified water.

Comparative Example 4

The prescription of Example 2 was emulsified by a desk homomixer LR-1 made by Mizuho Industry Co., Ltd. to prepare a cream.

Comparative Example 5

A polyethylene glycol (average molecular weight=6,000) in the prescription of Example 2 was replaced with 1,3-butylene glycol to prepare a cream.

Comparative Example 6

A 6% aqueous colloidal hydrous montmorillonite solution in the prescription of Example 2 was replaced with purified water.

With regard to these emulsions, Table 1 shows the results of observed states, average particle diameters (μm), the results after centrifugal separation, and the results of storage at a temperature of 50° C.

State of the cream:

Immediately after the preparation, the state of the cream was evaluated by the naked eye.

Average particle diameter:

An average particle diameter was measured by the use of a particle size distribution measuring apparatus (SALD-2000, made by Shimazu Seisakusho Ltd.).

State of the cream after centrifugal separation:

After the centrifugal separation at 6,000 rpm for 30 minutes, the state of the cream was evaluated by the naked eye.

Storage state at 50° C.:

The cream was placed in a thermostatic chamber at 50° C., and the change of the cream was observed with time.

TABLE 1

| | State | Average Particle Diameter (micron) | Centrifugal Separation | Storage Test at 50° C. |
|---|---|---|---|---|
| Example 1 | Creamy | 0.08 | Not separated | Stable for 3 months |
| Example 2 | Creamy | 0.07 | Not separated | Stable for 3 months |
| Comp. Ex. 1 | Softly Creamy | 1.02 | Separated | Separated after 6 days |
| Comp. Ex. 2 | Bad gloss | 0.37 | Separated | Separated after 12 days |
| Comp. Ex. 3 | Not creamy | — | Separated | Separated after 1 day |
| Comp. Ex. 4 | Softly Creamy | 0.97 | Not separated | Separated after 8 days |
| Comp. Ex. 5 | Bad gloss | 0.25 | Separated | Separated after 14 days |
| Comp. Ex. 6 | Not creamy | — | Separated | Separated after 1 day |

The creams obtained by emulsifying the prescriptions of the present invention with the aid of the microfluidizer could maintain a strong cream state.

In the case that the prescription of the present invention was used but the emulsification was not carried out by the microfluidizer, the resultant cream was separated by the centrifugal separation, and it was also separated in 6 days at 50° C. (Comparative Example 1).

In the case that the aqueous colloidal hydrous silicate solution was blended but the polyethylene glycol was replaced with 1,3-butylene glycol, the resultant cream was separated by the centrifugal separation, and it was also separated in 12 days at 50° C. and the gloss of the cream was bad (Comparative Example 2).

In the case that the aqueous colloidal hydrous silicate solution was not blended, any cream state could not be obtained. Separation took place at the time of the centrifugal separation, and the mixture was separated in 1 day at 50° C. (Comparative Example 3).

In the case that the prescription containing the crystalline cellulose of the present invention was emulsified by a homomixer instead of the microfluidizer, the resultant cream was separated by the centrifugal separation, and it was also separated in 8 days at 50° C. (Comparative Example 4).

In the case that the prescription containing the crystalline cellulose and the aqueous colloidal hydrous silicate solution was used but the polyethylene glycol was replaced with 1,3-butylene glycol, the resultant cream was separated by the centrifugal separation, and it was also separated in 14 days at 50° C. (Comparative Example 5).

In the case of the prescription containing the crystalline cellulose of Example 2 but not using the aqueous colloidal hydrous silicate solution, any cream state could not be obtained. Separation took place by the centrifugal operation, and the mixture was separated in 1 day at 50° C. (Comparative Example 6).

In the case that the prescription containing the colloidal hydrous silicate and the polyethylene glycol having an average molecular weight of 1,000–10,000 was emulsified with the aid of the microfluidizer, the resultant emulsion assumed a strong creamy state and had an average particle diameter of 0.1 μm or less. Furthermore, when subjected to the centrifugal separation, the emulsion was not separated, and it did not separate even after the storage at 50° C. for 3 months or more. In addition, since no surface active agent was used, the emulsion was safe for skin.

What is claimed is:

1. An oil-in-water type cream base comprising an oil phase and a water phase, said water phase comprising water, a colloidal hydrous silicate, and a polyethylene glycol, wherein said oil component is selected from the group consisting of squalane, solid oils, triglycerides, wax esters, and synthetic monoesters, said base being free of surfactant and being prepared by microfluidizer emulsification at a treatment pressure of at least 700 kg/cm$^2$.

2. An oil-in-water type cream base according to claim 1 wherein the amount of the colloidal hydrous silicate is in the range of 0.2 to 10.0% by weight based on the weight of an aqueous component, and the amount of the polyethylene glycol is in the range of 0.3 to 15.0% by weight based on the weight of the aqueous component.

3. An oil-in-water type cream base, according to claim 1, wherein said oil component is selected from the group consisting of squalene, jojoba oil, beeswax, whale wax, cetyl alcohol, stearyl alcohol, and octyldodecyl myristate.

4. An oil-in-water type cream base comprising an oil phase and a water phase, said water phase comprising water, a colloidal hydrous silicate, and a polyethylene glycol having an average molecular weight of 1,000–10,000, wherein said oil component is selected from the group consisting of squalane, solid oils, triglycerides, wax esters, and synthetic monoesters, said base being free of surfactant and being prepared by and emulsified by means of microfluidizer emulsification at a treatment pressure of at least 700 kg/cm$^2$.

5. An oil-in-water type cream base according to claim 4 wherein the amount of the colloidal hydrous silicate is in the range of 0.2 to 10.0% by weight based on the weight of an aqueous component, and the amount of the polyethylene glycol is in the range of 0.3 to 15.0% by weight based on the weight of the aqueous component.

6. An oil-in-water type cream base, according to claim 4, wherein said oil component is selected from the group consisting of squalene, jojoba oil, beeswax, whale wax, cetyl alcohol, stearyl alcohol, and octyldodecyl myristate.

7. An oil-in-water type cream base comprising an oil phase and a water phase, said water phase comprising water, a colloidal hydrous silicate, a polyethylene glycol having an average molecular weight of 1,000–10,000, and a crystalline cellulose, wherein said oil component is selected from the group consisting of squalane, solid oils, triglycerides, wax esters, and synthetic monoesters, said base being free of surfactant and being prepared by microfluidizer emulsification at a treatment pressure of at least 700 kg/cm$^2$.

8. An oil-in-water type cream base according to claim 7 wherein the amount of the colloidal hydrous silicate is in the range of 0.2 to 10.0 % by weight based on the weight of an aqueous component, and the amount of the polyethylene glycol is in the range of 0.3 to 15.0 % by weight based on the weight of the aqueous component.

9. An oil-in-water type cream base, according to claim 7, wherein said oil component is selected from the group consisting of squalene, jojoba oil, beeswax, whale wax, cetyl alcohol, stearyl alcohol, and octyldodecyl myristate.

10. An oil-in-water type cream base consisting of an oil phase and a water phase, said water phase consisting of water, a colloidal hydrous silicate, and a polyethylene glycol, wherein said oil component is selected from the group consisting of squalane, triglycerides, wax esters, and synthetic monoesters, said base being free of surfactant and being prepared by microfluidizer emulsification at a treatment pressure of at least 700 kg/cm$^2$.

11. An oil-in-water type cream base consisting of an oil phase and a water phase, said water phase consisting of water, a colloidal hydrous silicate, and a polyethylene glycol having an average molecular weight of 1,000–10,000, wherein said oil component is selected from the group consisting of squalane, triglycerides, wax esters, and synthetic monoesters, said base being free of surfactant and being prepared by and emulsified by means of microfluidizer emulsification at a treatment pressure of at least 700 kg/cm$^2$.

12. An oil-in-water type cream base consisting of an oil phase and a water phase, said water phase consisting of water, a colloidal hydrous silicate, a polyethylene glycol having an average molecular weight of 1,000–10,000, and a crystalline cellulose, wherein said oil component is selected from the group consisting of squalane, triglycerides, wax esters, and synthetic monoesters, said base being free of surfactant and being prepared by microfluidizer emulsification at a treatment pressure of at least 700 kg/cm$^2$.

* * * * *